United States Patent [19]

Indig et al.

[11] Patent Number: 5,217,596
[45] Date of Patent: Jun. 8, 1993

[54] ELECTRODE PROBE FOR USE IN AQUEOUS ENVIRONMENTS OF HIGH TEMPERATURE AND HIGH RADIATION

[75] Inventors: Maurice E. Indig, Fremont; William D. Miller, San Jose, both of Calif.

[73] Assignee: General Electric Company, San Jose, Calif.

[21] Appl. No.: 745,296

[22] Filed: Aug. 15, 1991

[51] Int. Cl.$^5$ ............................................. G01N 27/30
[52] U.S. Cl. ................................ 204/435; 376/245; 376/256; 204/400
[58] Field of Search ................. 376/245, 256, 306; 338/28, 30, 233, 229; 204/435, 400

[56] References Cited

U.S. PATENT DOCUMENTS

| | | | |
|---|---|---|---|
| 4,320,378 | 3/1982 | Taniguchi et al. | 338/34 |
| 4,636,292 | 1/1987 | Fejes et al. | 204/404 |
| 4,948,492 | 8/1990 | Niedrach et al. | 204/435 |
| 4,978,921 | 12/1990 | Indig et al. | 324/446 |
| 4,990,855 | 2/1991 | Niedrach et al. | 324/449 |
| 5,043,053 | 8/1991 | Indig et al. | 204/421 |

Primary Examiner—Donald P. Walsh
Assistant Examiner—Chrisman D. Carroll
Attorney, Agent, or Firm—Robert R. Schroeder

[57] ABSTRACT

An electrode probe suited for employment as an electrical potential reference electrode in an aqueous, high pressure, high temperature, and high radiation field environment such as the core of a nuclear reactor is described. The electrode is a brazed and welded assembly consisting of only ceramic and metal parts including a sapphire base which is brazed to a kovar/stainless steel housing, welded in turn, to a coaxial cable assembly for signal transfer. The base incorporates an integrally formed pedestal through which a conductor wire extends and over which is positioned a selectively coated cylindrically shaped sealing retainer. The device is particularly suited for employment with a silver/silver chloride electrode system.

20 Claims, 2 Drawing Sheets

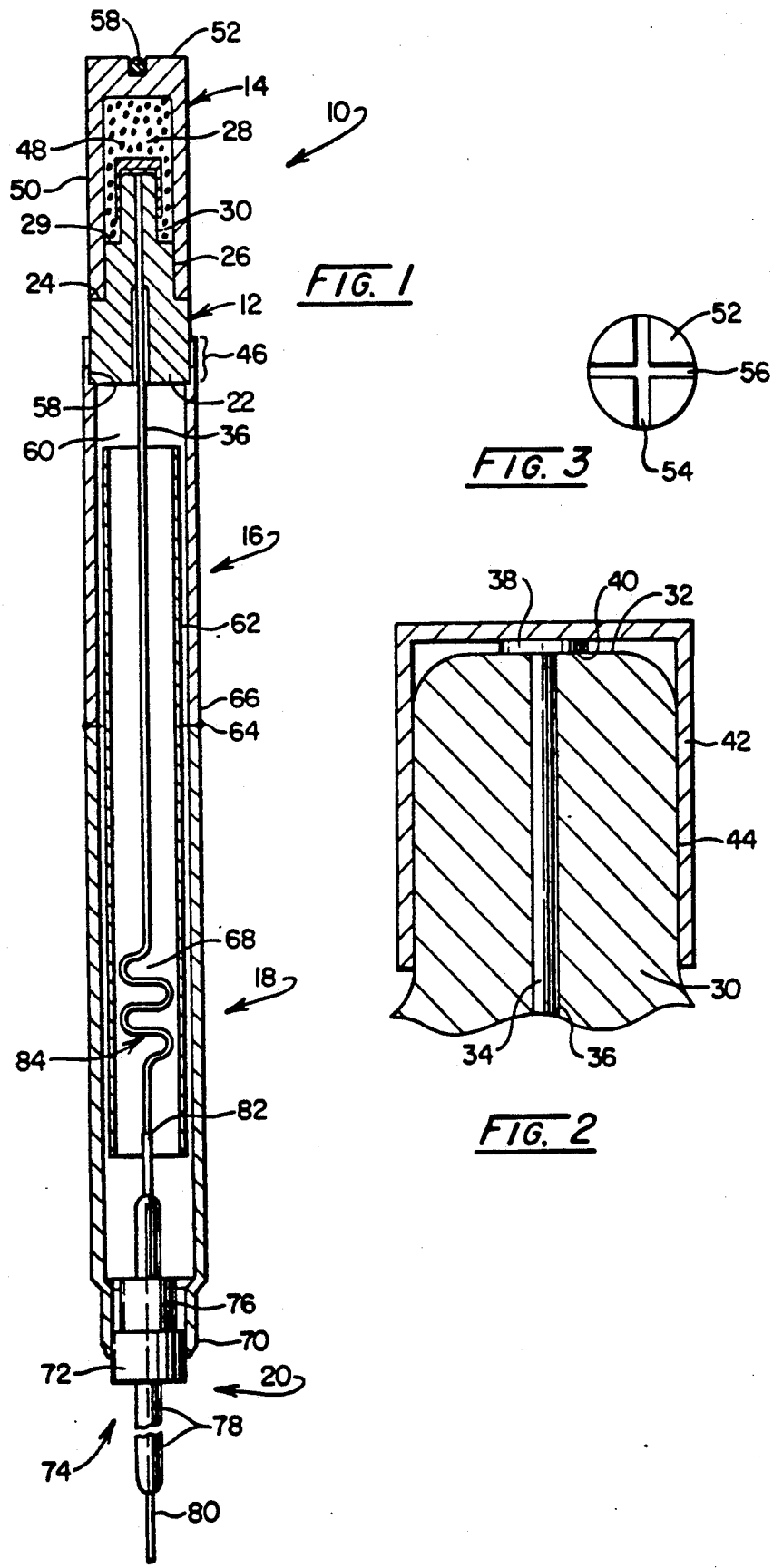

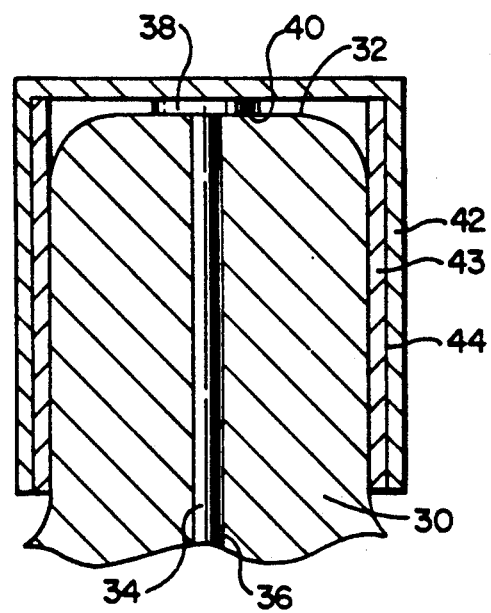

ELECTRODE PROBE FOR USE IN AQUEOUS ENVIRONMENTS OF HIGH TEMPERATURE AND HIGH RADIATION

BACKGROUND OF THE INVENTION

The nuclear power industry long has been engaged in a multitude of studies and investigations seeking improvement in the stamina and reliability of the materials and components forming a reactor based power system. One such investigation has been concerned with intergranular stress corrosion cracking (IGSCC) which heretofore principally has been manifested in the water recirculation piping systems external to the radiation intense reactor core regions of nuclear facilities. Typically, the piping architecture of these external systems is formed of a stainless steel material. Generally, these studies have determined that three factors must occur in coincidence to create IGSCC promotional conditions. These factors are: (a) a sensitization of the metal (stainless steel), for example, such as caused by a chromium depletion at grain boundaries which may be caused by heat treatment in the course of normal processing of the material or by welding and like procedures; (b) the presence of tensile stress in the material; and (c) the oxygenated normal water chemistry (NWC) environment typically present in a boiling water reactor (BWR). This latter environment is occasioned by any of a variety of oxidizing species contributed by impurities in reactor coolant water. By removing any one of these three factors, the IGSCC phenomenon is essentially obviated. Such removal particularly has been accomplished with respect to the latter, oxygenated environment factor through employment of an electrochemical potential monitoring approach combined with an associated hydrogen water chemistry (HWC) technique providing for a controlled addition or injection of hydrogen into the aqueous coolant environment.

Electrochemical potential monitoring is carried out employing paired electrochemical half-cell probes or electrodes which are mounted within the recirculation piping or in an external vessel which has its water source from the reactor water in the recirculation piping. The electrodes are accessed to the external environment through gland type mountings or the like. Where, as in the instant application, the electrode system of interest involves the potential from a metal corrosion electrode, then the reference electrode can conveniently be a metal-insoluble salt electrode, if the metal-salt couple is chemically stable and if appropriate thermodynamic data is available. Accordingly, one of the thus-mounted probes which is configured as a reference electrode may be based, for example, on a silver/silver chloride half-cell reaction. Once the reference electrode half-cell is defined, the cell is completed with the sensing cell portion based upon a metal such as platinum or stainless steel. Verification of the reference electrode and/or the electrode pair is carried out by thermodynamic evaluation and appropriate Nernst based electrochemical calculations in combination with laboratory testing within a known environment.

Half cell electrodes developed for use in reactor circulation piping traditionally have been configured with metal housings, high temperature ceramics, and polymeric seals such as Teflon brand polytetrafluoroethylene. These structures have performed adequately in the more benign and essentially radiation-free environments of recirculation piping.

Over the recent past, investigators have sought to expand the electrochemical potential (ECP) monitoring procedures to the severe environment of the fluid in the vicinity of the reactor core itself for the purpose of studying or quantifying the effect of hydrogen-water chemistry adjustment in mitigating irradiation assisted stress corrosion cracking (IASSC) as well as IGSCC. Within the reactor core, the monitoring electrode can be mounted, for example, with otherwise unemployed or in tandem with the traveling instrumentation probe (TIP) of available local power range monitors (LPRM) and the like. The monitors are located in a severe, high temperature (550° F.), high radiation (typically $10^9$ R (rads) per hour gamma, $10^{13}$R per hour neutron) water environments. Probe structures of earlier designs are completely inadequate for this reactor core environment, both from a material standpoint and with respect to the critical need to prevent leakage of radioactive materials to the environment outside of the reactor vessel. One probe, however, that has a robust structure adequate for use in the rigorous environment of the reactor core of a nuclear power facility is disclosed in commonly-assigned U.S. Ser. No. 07/345,740, filed May 1, 1989, now U.S. Pat. No. 4,948,492. A critical feature of such probe design is the alumina (sapphire) post and post cap which are located inside of the base. Because of space limitations, the manufacturing processes which are performed inside the base, such as metalizing and brazing, cannot be controlled to ensure a reproducible, high quality product. Inadequate metalizing and brazing at this interface often may not be detected until the electrode fails prematurely either during final testing or in service in a reactor.

BROAD STATEMENT OF THE INVENTION

The present invention is addressed to a reference electrode probe for evaluating electrochemical potentials and the like, which probe has a robust structure particularly suiting it for employment within the rigorous environment of the reactor core of a nuclear power facility. Half-cell electrode components are positioned within a single crystal alumina (sapphire) retainer or base. The base is formed from an alumina rod and an alumina end cap. The alumina rod has a base region with an externally disposed surface attachment region. The rod further comprises an adjacent land and sidewall end cap surface attachment region and an integrally-formed pedestal disposed radially-inwardly and in spaced-apart relationship from said rod sidewall. The pedestal has a continuous access channel extending through the base region and the pedestal. The alumina end cap has a base and sidewalls extending to an opening therefrom for defining an internally-disposed cavity. The access opening is positioned in sealed brazed connection with the rod land and the end cap sidewalls adjacent said access opening are positioned in sealed braze connection with the rod sidewall for said end cap cavity to contain said pedestal. A metal salt electrochemical reactant is located within the cavity. Electrical communication to the cavity retained reactant is provided by a conductor which is positioned within the access channel. A cylinder with a cap coated with a metal component, i.e. silver, of the half-cell is positioned over and intimately compressively bonded and sealed over the pedestal and is in electrical contact with a conductor to form the internal seal which has a high level of integrity. For achieving a compatibility of thermal expansion, the sealing retainer is formed of a kovar material having appropriate sintered coatings thereon. It also is possible to utilize a platinum retainer or a combination of a platinum and kovar in order to take advantage of eliminating any extraneous chemical reactions. At the distal end of the sapphire rod, a kovar transition member is sealed by appropriate silver brazing to the sapphire rod to provide a seal and this kovar sleeve is supported by a positioning and signal transfer arrangement including a stainless steel transition piece which, in turn, is sealed to a cable connector assembly.

Advantages of the present invention include an electrode probe that is designed for use within the rigorous environment of the reactor core of a nuclear power facility. Another advantage is a design that permits inspection and quality control procedures to be exercised over critical components at all stages of manufacturing and testing. A further advantage is the ability to visually examine the critical features of the probe design after each manufacturing process and to examine the final product for improved quality control and performance of the electrode probe. These and other advantages will be readily apparent to those skilled in the art based upon the disclosure contained herein.

BRIEF DESCRIPTION OF THE DRAWINGS

FIG. 1 is a sectional view of an electrode probe according to the present invention;

FIG. 2 is a partial sectional view of the sealing retainer structure shown in FIG. 1;

FIG. 3 is an end view of the electrode probe shown in FIG. 1: and

FIG. 4 is an alternative platinum cap arrangement for use with the inventive electrode probe.

The drawings will be described in detail in connection with the following description of the invention.

DETAILED DESCRIPTION OF THE INVENTION

While having utility in a broad variety of industrial monitoring functions, the electrode structure of the instant invention finds particular utility operating under the rigorous environment of the reactor core of a nuclear power facility. No elastomeric seals or polymeric components are present in its structure which incorporates a sealing architecture of the highest integrity. In the latter regard, a brazed and welded assembly consisting only of ceramic and metal parts forms the structure of the device. The electrode finds preferable employment as a reference component of an electrode system involving a metal-metal ion couple and thus the instant electrode can conveniently be a metal, slightly soluble salt electrode. For the embodiment shown, the device is a silver-silver chloride reference which functions reversibly. In general, these electrodes consist of a silver metal with silver chloride immersed in a solution containing chloride anions. The electrode reaction is:

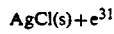
$AgCl(s) + e^-$

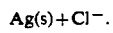
$Ag(s) + Cl^-$.

At 25° C., the electrochemical chemical potential of such an electrode can be computed as:

$$V(SHE) = 0.2222 - 0.05915 \log_{10} a_{Cl^-},$$

where V(SHE) means the voltage of the electrode of interest versus the standard hydrogen electrode. For a more detailed discussion in connection with the above, reference is made to *Physical Chemistry* by G. W. Castellan, Chapter 17, "Equilibria in Electrochemical Cells", pp 344–382, Addison-Wesley Publishing Co., Reading, Mass. (1964).

Referring to FIG. 1, the structure of the reference electrode according of the invention is represented in general at 10 in sectional fashion. Probe 10 has a generally cylindrical structure comprised of five principal components including a cylindrically shaped cell retainer or base 12; a cylindrical end cap formed over base 12 as at 14; and a positioning and transfer arrangement which includes: base sleeve 16; elongate cylindrical transition component or piece 18; and cable assembly or connector 20.

Retainer or base 12 is structured not only to withstand the duress otherwise imposed by radiation, high temperatures, and pressure, but also to achieve a highly reliable seal to avoid the incursion of reactor coolant water through the electrode and ultimately to the outside environment. The base, in its preferred embodiment, is formed of sapphire which is a single crystal form of alumina. The sapphire material not only provides requisite electrical insulation and is chemically inert, but also by virtue of its single crystal structure, provides no grain boundaries which could be attacked by the universal solvent, water. Thus, there is no intergrannular penetration into the material even though there will be some general corrosion attack. Accordingly, the material forming base 12 is ideal for the in-core environment. Other materials will occur to those art skilled, for example high purity alumina or ruby.

Base 12 is formed having cylindrical base region 22 which is terminated at its upper end by cylindrical land 24 which is adjacent to cylindrical sidewall 26. Adjacent land 24 and sidewall 26 form an end cap surface attachment region. Pedestal 30 is adjacent to land 29 which is disposed at the end of sidewall 26 opposite land 24. Pedestal 30 is integrally formed from base 12.

Referring additionally to FIG. 2, pedestal 30 is seen to extend within cavity 28 from base region 22 to flat coupling surface 32. Cylindrical bore or continuous access channel 34 extends from coupling surface 32 and through base region 22. Channel 34 serves to provide access for electrically conductive transmission line or conductor wire 36 which may be formed of kovar and flattened at its end position 38 in disk or nail head shaped fashion. Wire 36 is seen to be inserted through channel 34 and inward side 40 of disk or material 38 is shown in abutting contacting adjacency with coupling surface 32. Kovar materials are a group of alloys having a characteristic of thermal expansion making it compatible with that of the alumina materials of base 12. One representative kovar material comprises Fe 53.8%, Ni 29%, Co 17%, and M n 0.2% (Hackh's Chemical Dictionary, Fourth Edition, page 374, McGraw-Hill, Inc., 1969). Heretofore, this group of alloys were employed in radio tube and thermostat construction where bonding to glass was required. Kovar alloys have been known for quite some time. Broadly, they contain from 17–18% cobalt, 28–29% nickel, with the balance being mostly iron. Their ductility and lack of embrittlement under conditions of ordinary use including heating and annealing make them useful, such as in sealing glasses, as further expounded upon by Kohl in *Electron Tubes*, pp. 448 et. seq.

The first of the internal seals for electrode 10 is developed with respect to the necessary electrical communication provided by wire 36 through the employment of pedestal 30 in conjunction with sealing retainer or post cap 42 which also is fashioned of kovar. Retainer 42 is formed as a cylinder having a closed end and exhibiting an internal diameter serving to provide an outwardly disposed seal at its union with vertical surface 44 of pedestal 30. To achieve a sealed union of high integrity between the concave internal surface of cap 42 and outer surface of pedestal 30, certain metallurgical procedures are carried out. In this regard, the surface of pedestal 30 is metalized by painting it with a tungsten paint, following which it is inspected and then fired employing conventional procedures. This fired surface then is inspected and the thus-metalized region is nickel-plated, following which the thus-metalized regions are nickel-plated and sintered. Alternatively, platinum plating may be employed on the metalized surface followed by sintering, or platinum plating may be employed following nickel plating and sintering. The sintered surface then is inspected.

Kovar cap 42 also is subjected to a somewhat elaborate procedure of surface treatment in view of its presence within a silver chloride environment, which is a strong oxidizing agent. It also will be observed that the ultimate coating is silver which forms part of the electrode system. In preparation of this machined cup-like part, it first is cleaned and inspected, following which it undergoes a nickel strike. The cup-like structure is sintered to improve the plating bond, whereupon the sintered part is again inspected. Alternatively, it also is possible to platinum plate and sinter directly on the cleaned kovar cap, or platinum plate on the nickel strike or nickel plating. Rhodium plating may be substituted for platinum plating. After each plating or sintering operation, inspections are required to assure continuity of the separate platings.

Component 42 then is silver-plated and the silver-plating is sintered following which an inspection procedure takes place. Component 42 again is silver-plated as a last step in its treatment. An alternate arrangement for cap 42 may be employed as set forth at FIG. 4. In this alternate arrangement, platinum rather than kovar is used for fabricating cap 42. However, inner annulus 43 is joined by silver brazing to cylinder wall 44 as illustrated at FIG. 4. Kovar annulus or ring 43 first is cleaned and plated with silver in preparation to joining to cylinder wall 44. Platinum cap 42 also is cleaned and plated with silver, and sintered. A second silver plating and sintering also may be employed. In the assembly of this sealing arrangement, disk component 38 of conductor 34 is spot welded or brazed to the underside of the top surface of cap 42. Additionally, cap 42 is sealably attached to the surface of pedestal 30 by silver brazing at vertical interface 44. Additional amounts of silver braze may be applied during brazing to provide a thicker coating of silver on the retainer cap and also may fill the gap between pedestal 30 and cylinder wall 44.

Returning to FIG. 1, the lower, outer cylindrical surface portion of base region 22 of base 12 is a surface attachment region, the extent of which is represented by bracket 46. This region also is metalized and nickel plated in the same manner as the surface of pedestal 30 in order to provide a next seal in the electrode architecture.

Shown positioned within cavity 28 of end cap 14 and retainer 12 is a pellet of silver chloride which herein is shown schematically in granular form as an aqueous suspension as represented at 48. In a preferred arrangement, the silver chloride may be melted and formed into rods, portions or plugs of which then may be located within cavity 28.

End cap 14 also is formed of sapphire, the single crystal form of alumina and may, for example, be fashioned of a noted alternate material. Cap 14 is cup-like in shape being formed of generally cylindrical sidewall 50 and base 52. The cap is dimensioned so as to provide a "tight" fit around base 12 at land 24 and sidewall 26. The noted fit is one which permits electrolytic communication of the reactor coolant water with a very minimum movement or mass transfer of water or material. In effect, a diffusion junction is formed between cap 14 and land 24/sidewall 26. Exemplary of the type of fit involved, the access opening diameter may, for example, be machined to provide a gap of only 0.0005 in. Further retention of end cap 14 is provided by transverse slots 54 and 56 (see FIG. 3) within which stainless steel wire, shown in section at 58, is positioned thereabout in harness fashion and attachment at lower connector 20 region of device 10. Alternatively, straps of proper dimension may be fitted into slots 54 and welded to kovar sleeve 16.

Base or retainer 12 of device 10 is initially supported by cylindrical base sleeve 16 which, to achieve compatibility with sapphire base 12 from the standpoint of the thermal coefficient of expansion thereof, is formed also of kovar or alloy 42. Note that the internal diameter of sleeve 16 is offset, for example, by counterboring at 58 to provide an acceptance portion suited for receiving and being attached to surface attachment region 46 of base region 22 of base 12 for forming an intimate seal thereat. The initially produced cylinder of kovar for sleeve 16 is prepared by initially cleaning and inspecting it, following which a post machine annealing procedure is carried out. Following this annealing procedure, the component is nickel-plated and that nickel-plating and sintering procedure then is carried out, followed by a next inspection. Generally, the thus-prepared component is stored in sealed plastic packaging until it is utilized. Attachment development of an intimate seal of surface attachment region 46 of base 12 with the acceptance portion 58 of sleeve 16 is provided by silver brazing. This arrangement then completes a highly secure second seal for electrode 10 as is required in view of the intended use thereof within the core region of a reactor. Hollow interior 60 of cylindrical (annular) sleeve 16 provides an internal channel through which wire or conduit 36 may pass. To assure that wire 36 is insulated from the internal surfaces of sleeve 16, alumina tube 62 is inserted within channel 60. Annular ceramic tube 62 provides such insulation while remaining immune from the temperatures encountered with the intended use of device 10.

Kovar sleeve 16 is supported, in turn, by attachment to cylindrical transition component 18 which, for the instant application, may be formed of a type 304 stainless steel. Transition piece 18 is of corresponding diametric extent as sleeve 16 and is attached at its transition end 64 to corresponding attachment surface 66 thereof utilizing a tungsten inert gas weld (TIG) as applied, for example, by a tube welder. Hollow interior 68 of transition tube 18 provides an internal channel representing a continuation of channel 60 of sleeve 16. Alumina tube 62 is seen to extend continuously thereinto. The lower end of transition tube 18 is formed in necked-down fashion to provide sealing end 70. End 70 is welded by the noted tungsten inert gas welding technique to cylindrical stainless steel collar 72 of a cable connector assembly represented generally at 74 and which is shown having ceramic support component 76 through which mineral insulated cable 78 extends. Cable 78 may be provided having a stainless steel outer shell within which the noted mineral insulation may be provided as alumina and centrally disposed within which is conducting cable 80. Mineral insulated cable 78 extends outwardly to the ambient environment from the reactor environment region in the application of interest. To provide an electric circuit completing connection with lead 80, nickel or kovar conductor 36 is spot welded thereto at 82. To facilitate this attachment and provide a modicum of tension within the nickel or kovar conductor 36, a spring winding is formed in connector 36 as represented in general at 84. Cable assembly 74 is marketed, for example, by Reuter-Stokes, a division of General Electric Company, Twinsburg, Ohio.

Since certain changes may be made in the above-described apparatus without departing from the scope of the invention herein involved, it is intended that all matter contained in the description thereof or shown in the accompanying drawings shall be interpreted as illustrative and not in a limiting sense.

We claim:
1. A reference electrode probe for employment in monitoring electrochemical potentials, comprising:
   (a) an alumina base having a base region with an externally disposed surface attachment region, an adjacent land and sidewall end cap surface attachment region, an integrally-formed pedestal disposed radially-inwardly and in spaced-apart relationship from said base sidewall, said pedestal having a continuous access channel extending through said base region and said pedestal;
   (b) an alumina end cap having a base and sidewall extending to an access opening therefrom for defining an internally-disposed cavity, said access opening positioned in sealed connection with said base and the end cap sidewalls adjacent said access opening positioned in sealed braze connection with said base sidewall for said end cap cavity to contain said pedestal;
   (c) an electrically conductive sealing cap electrode, formed as a cylinder with a closed end and having an interior surface positioned over said pedestal in closely nesting adjacency and sealably fixed thereto;
   (d) a metal salt electrochemical reactant located and sealed within said cavity;
   (e) a first annular metal sleeve formed of a metal exhibiting a coefficient of expansion compatible with said alumina base, having an alumina retainer region in sealing engagement with said base sleeve attachment region, said sleeve having an oppositely disposed outlet;
   (f) a first insulated electrical conductor in electrical connection with said sealing cap electrode and extending through said base access channel and through said annular metal sleeve to said sleeve outlet; and
   (g) a positioning and signal transfer assembly associated with said sleeve outlet for providing support for said sleeve and for conveying electrical signals from said conductor.

2. The electrode probe of claim 1 in which said positioning and signal transfer means comprises:
   a transition component formed of a second select metal and having a second internal channel extending therethrough to a sealing end and sealably connected with said sleeve;
   said first conductor extending into said second internal channel; and
   cable connector means having a collar weldably attached and sealed to said transition component sealing end and having a second conductor extending therethrough for connection with said first conductor.

3. The electrode probe of claim 1 in which said alumina cell base is formed from a single crystal sapphire.

4. The electrode probe of claim 1 in which said sealing cap electrode is formed of kovar, the surface of which is an intimately adhered coating of said electrode metal.

5. The electrode probe of claim 1 in which said first conductor includes an integrally formed disk or nail head positioned upon said pedestal over said access channel and electrically coupled with said base interior surface.

6. The electrode probe of claim 1 in which said sleeve is formed of kovar.

7. The electrode probe of claim 2 in which said transition component is formed of stainless steel and is welded to said sleeve to form a continuous internal channel from said first and second internal channels.

8. The electrode probe of claim 7 including an elongate annular alumina insulator located within said continuous internal channel for electrically insulating said first conductor.

9. The electrode probe of claim 1 in which said first conductor is kovar or nickel wire.

10. A reference electrode probe for employment in monitoring electrochemical potentials, comprising:
   (a) a cylindrically-shaped alumina base having a base region with an externally disposed surface attachment region, and adjacent land and sidewall end cap surface attachment region, an integrally-formed pedestal disposed radially-inwardly and in spaced-apart relationship from said base sidewall, said pedestal having a continuous access channel extending through said base region and said pedestal, a first metallic coating intimately adhered to the externally disposed surface of said pedestal, a second metallic coating intimately adhered to said base externally disposed surface attachment region;
   (b) a sealing retainer, formed as a cylinder with a closed end, having an externally disposed silver coating, and having an interior surface positioned over said pedestal in closely nesting adjacency and sealably fixed thereto;
   (c) an alumina end cap having a base and sidewall extending to an access opening therefrom for defining an internally-disposed cavity, said access opening positioned in sealed connection with said base and the end cap sidewalls adjacent said access opening positioned in sealed braze connection with said base sidewall for said end cap cavity to contain said pedestal;
   (d) silver chloride salt located and sealed within said cavity for providing, with said cap silver coating, the components of a metal-salt electrode;

(e) a first kovar annular metal sleeve having an alumina base region in sealing engagement with said base sleeve attachment region, said sleeve having an oppositely disposed outlet;

(f) a stainless steel annular cylindrical transition component having a second internal channel extending from the transition end to sealing end and weldably connected at said transition end in fluid sealing relationship with said sleeve attachment surface;

(g) a cable connector having a metal collar weldably attached and sealed to said transition component sealing end and having a first electrical conductor extending therethrough for communication with said second internal channel; and (h) a second electrical conductor coupled with said first electrical conductor and insulatively extending through said first channel, second channel, and said continuous access channel for electrical contact with said sealing base interior surface.

11. The reference electrode probe of claim 10 in which said alumina cell base is single crystal sapphire.

12. The reference electrode probe of claim 10 in which said sealing retainer is formed of kovar metal, the surface of which is covered with a sequence of coatings including sintered nickel plate, sintered rhodium or platinum plate, and sintered silver plate.

13. The reference electrode probe of claim 12 in which said pedestal first metallic coating is provided as a sequence of coatings including a fired, metallized surface which is covered with a sintered nickel plate, and optionally one or more of sintered rhodium plate, sintered platinum plate, followed by sintered silver plate.

14. The reference electrode probe of claim 13 in which said sealing retainer is fixed to said pedestal with a silver braze.

15. The reference electrode probe of claim 13 in which said second conductor includes an integrally formed disk or nail head positioned upon said pedestal flat coupling surface over said access channel and brazingly coupled to said sealing retainer interior surface.

16. The reference electrode probe of claim 10 including an annular alumina tube located within said first and second channels through which said second conductor extends for effecting the insulation thereof.

17. The reference electrode probe of claim 10 in which said alumina base externally disposed surface attachment region is nestably positioned within said sleeve means acceptance portion and is sealed thereto with a silver braze.

18. The reference electrode probe of claim 10 in which said alumina base externally disposed attachment region second metallic coating is provided as a sequence of coatings including a fired, metalized surface coating which is covered with a sintered nickel plate, over which optionally is formed a sintered silver plate.

19. The reference electrode probe of claim 10 in which said sleeve means is covered with a sintered nickel plate coating.

20. The reference electrode of claim 10 in which said sealing retainer is formed of a platinum cap and an internally-disposed kovar annulus, said kovar annulus being plated with silver and joined to the vertical internal surface of the platinum cap over which is formed sintered silver plate.

* * * * *